(12) United States Patent
Tzortzis et al.

(10) Patent No.: US 11,065,268 B2
(45) Date of Patent: Jul. 20, 2021

(54) METHOD OF PREVENTING DIARRHOEA

(75) Inventors: Georgios Tzortzis, Reading (GB); Glenn R. Gibson, Reading (GB)

(73) Assignee: CLASADO RESEARCH SERVICES LIMITED, Reading (GB)

( * ) Notice: Subject to any disclaimer, the term of this patent is extended or adjusted under 35 U.S.C. 154(b) by 0 days.

(21) Appl. No.: 13/322,430

(22) PCT Filed: May 27, 2009

(86) PCT No.: PCT/GB2009/001329
§ 371 (c)(1),
(2), (4) Date: Feb. 8, 2012

(87) PCT Pub. No.: WO2010/136742
PCT Pub. Date: Dec. 2, 2010

(65) Prior Publication Data
US 2012/0157406 A1 Jun. 21, 2012

(51) Int. Cl.
*A61K 31/7016* (2006.01)
*A61K 31/702* (2006.01)

(52) U.S. Cl.
CPC ........ *A61K 31/7016* (2013.01); *A61K 31/702* (2013.01)

(58) Field of Classification Search
CPC .......................... A61K 31/702; A61K 31/7016
USPC ......... 514/54, 61, 53, 23; 536/123.1, 123.13
See application file for complete search history.

(56) References Cited

U.S. PATENT DOCUMENTS

| | | | |
|---|---|---|---|
| 4,435,389 A | 3/1984 | Mutai et al. | |
| 4,873,229 A * | 10/1989 | Deya et al. | 514/54 |
| 4,944,952 A | 7/1990 | Kobayashi et al. | |
| 5,149,640 A | 9/1992 | Oonishi et al. | |
| 5,294,546 A | 3/1994 | Dombou et al. | |
| 6,555,348 B2 | 4/2003 | Jorgensen | |
| 7,883,874 B2 | 2/2011 | Gibson et al. | |
| 8,030,049 B2 | 10/2011 | Tzortzis et al. | |
| 8,058,047 B2 | 11/2011 | Tzortzis et al. | |
| 8,168,414 B2 | 5/2012 | Tzortzis et al. | |
| 2002/0086358 A1 | 7/2002 | Jorgensen et al. | |
| 2004/0131659 A1 | 7/2004 | Gibson et al. | |
| 2008/0199444 A1 | 8/2008 | Cui | |
| 2012/0157406 A1 | 6/2012 | Tzortzis et al. | |

FOREIGN PATENT DOCUMENTS

| | | |
|---|---|---|
| AU | 2003294835 | 6/2004 |
| EP | 0 089 940 A1 | 9/1983 |
| EP | 0 438 182 | 7/1991 |
| EP | 1 227 152 A1 | 7/2002 |
| GB | 2 412 380 B | 11/2005 |
| JP | 62059290 | 3/1987 |
| JP | 3049692 | 3/1991 |
| JP | 3049693 | 3/1991 |
| JP | 3246296 | 11/1991 |
| JP | 5-146273 | 6/1993 |
| JP | 5-146296 | 6/1993 |
| JP | 7089976 | 4/1995 |
| JP | 9121853 | 5/1997 |
| JP | 10023898 | 1/1998 |
| WO | WO 88/08025 | 10/1988 |
| WO | WO 96/06924 | 3/1996 |
| WO | WO 2000/033854 A | 6/2000 |
| WO | WO 00/46345 | 8/2000 |
| WO | WO 01/90317 A2 | 11/2001 |
| WO | WO 2004/052121 A1 | 6/2004 |
| WO | WO 2004/074496 A1 | 9/2004 |
| WO | WO 2005/003329 A1 * | 1/2005 |
| WO | WO 2005/003329 AI | 1/2005 |
| WO | WO 2007/054459 A2 | 5/2007 |
| WO | WO 2010/023422 A1 | 3/2010 |

OTHER PUBLICATIONS

Merriam-Webster's Third New International Dictionary, Dec. 2000.*
Fujiwara et al. (Applied and Environmental Microbiology (1997), 63(2), 506-512).*
Lomax et al. (Current pharmaceutical design, (2009) vol. 15, No. 13, pp. 1428-1518) (abstract sent).*
Searle et al. (Journal of Medical Microbiology (2009), 58, 37-48).*
McFarland et al. (Travel Medicine and Infectious Disease (2007) 5, 97-105).*
Hilton et al. (J Travel Med 1997; 4;41-43).*
Yates et al. (American Family Physician; Jun. 1, 2005, vol. 71, No. 11, pp. 2095-2100).*
Yang et al. (Jilin Nongye Daxue Xuebao (2004), 26(2), 197-200) (abstract sent).*
Albersheim, P., et al., "A Method for the Analysis of Sugars in Plant Cell-Wall Polysaccharides by Gas-Liquid Chromatography", Carbohydrate Research, 1967, vol. 5, pp. 340-345.
An, G.H., et al., "Isolation of Phaffia Rhodozyma Mutants with Increased Astaxanthin Content", Applied and Environmental Microbiology, Jan. 1989, pp. 116-124, vol. 55, No. 1.
Blakeney, A.B., et al., "A Simple and Rapid Preparation of Alditol Acetates for Monosaccharide Analysis", Carbohydrate Research, 1983, vol. 113, pp. 291-299, Elsevier Scientific Publishing Co., Netherlands.
Blanchette, D., et al., "α- and β-Galactosidase properties of Bifidobacterium infantis", Milchwissenschaft, vol. 47, No. 1, 1992, pp. 18-21.
Branden, C., et al., "Introduction to Protein Structure, Prediction, Engineering, and Design of Protein Structures", Garland Publishing, Inc. (1991), 3 pages.
Carpita, N. C., et al., "Linkage Structure of Carbohydrates by Gas Chromatography-Mass Spectrometry (GC-MS) of Partially Methylated Alditol Acetates", Analysis of Carbohydrates by GLC and MS (1989), pp. 157-216.

(Continued)

*Primary Examiner* — Shaojia A Jiang
*Assistant Examiner* — Michael C Henry
(74) *Attorney, Agent, or Firm* — Lewis Roca Rothgerber Christie LLP

(57) ABSTRACT

The present invention provides a method for the prevention of the incidence of and/or a reduction in the duration of acute diarrhoea, particularly in travelers, said method comprising orally administering an oligosaccharide composition, in particular a non-digestible oligosaccharide, to a mammal.

3 Claims, No Drawings

(56) References Cited

OTHER PUBLICATIONS

Ciucanu, I., et al., "A Simple and Rapid Method for the Permethylation of Carbohydrates", Carbohydrate Research, 1984, vol. 131, pp. 209-217, Elsevier Science Publishers B.V. Amsterdam, Netherlands.

Chabaud, M., et al., "Contribution of Interleukin 17 to Synovium Matrix Destruction in Rheumatoid Arthritis", Cytokine, vol. 12, No. 7, Jul. 2000, pp. 1092-1099.

Crittenden, R.G., "Prebiotics", Probiotics: A Critical Review; ISBB 1-898486-15-8 (1999), pp. 141-157, Horizon Scientific Press, Wymondham, U.K.

Doares, S.H., et al., "An Improved Method for the Preparation of Standards for Glycosyl-Linkage Analysis of Complex Carbohydrates", Carbohydrate Research, 1991, vol. 210, pp. 311-317, Elsevier Science Publishers B.V., Amsterdam.

Dumortier, V., et al., "Purification and Properties of a β-D-Galactosidase from Bifidobacterium Bifidum Exhibiting a Transgalactosylation Reaction", Biotechnol. Appl. Biochem., 19 (1994), pp. 341-354, Great Britain.

Dumortier, V., et al., "Primary Structure of Ten Galactosides Formed by Transglycosylation During Lactose Hydrolysis by Bifidobacterium Bifidum", Carbohydrate Research, vol. 201, 1990, pp. 115-123, Elsevier Science Publishers B.V., Amsterdam, Netherlands.

Gibson, G.R., et al., "Dietary Modulation of the Human Colonic Microbiota: Introducing the Concept of Prebiotics", Critical Review (1995), pp. 1401-1412, American Institute of Nutrition.

Gibson, G.R., "Bifidobacteria and Oligosaccharides—The Functional Use of Prebiotics", Positive Nutrition: Functional Foods; IBC Technical Services (1995), 34 pages, London.

Gibson, G.R., et al., "Prebiotics: New Developments in Functional Foods" Chandos Publishing, Oxford, 2000, 96 pages.

Gopal, P.K., et al., "Utilisation of Galacto-Oligosaccharides as Selective Substrates for Growth by Lactic Acid Bacteria Including Bifidobacterium Lactis DR10 and Lactobacillus Rhamnosus DR20", International Dairy Journal 11 (2001), pp. 19-25, Elsevier Science Ltd.

Goulas, A et al., "Development of a process for the production and purification of α- and β-galactooligosaccharides from Bifidobacterium bifidum NCIMB 41171", International Dairy Journal, vol. 17, No. 6, Jun. 2007, pp. 648-656, XP002431977.

Hanatani, M., et al., "Physical and Genetic Characterization of the Melibiose Operon and Identification of the Gene Products in *Escherichia coli*"; The Journal of Biological Chemistry, Feb. 10, 1984, vol. 259, No. 3, pp. 1807-1812.

Hashimoto, H., et al., "Candida Guilliermondii H-404", Journal of Applied Glycoscience (1994), pp. 143-150, vol. 41, No. 2.

Hashimoto, H., et al., "Production of the Positional Isomers of a-Galactobiose by the Reverse Reaction of α-Galactosidase from Candida Guilliermondii H-404", Journal of Applied Glycoscience (2001), pp. 279-285, vol. 48, No. 3.

Hung, M.N., et al., "Molecular and Biochemical Analysis of Two β-Galactosidases from Bifdobacterium Infantis HL96", Applied and Environmental Microbiology, Sep. 2001, pp. 4256-4263, vol. 67, No. 9, American Society for Microbiology.

Ito, M., et al., "Effects of Administration of Galactooligosaccharides on the Human Faecal Microflora, Stool Weight and Abdominal Sensation", Microbial Ecology in Health and Disease, 1990, vol. 3, pp. 285-292, John Wiley & Sons, Ltd.

Ito, M., et al., "Effects of Transgalactosylated Disaccharides on the Human Intestinal Microflora and their Metabolism", J. Nutr. Sci. Vitaminol (1993), vol. 39, pp. 279-288.

Karlsson, K., "Animal Glycosphingolipids as Membrane Attachment Sites for Bacteria", Annu. Rev. Biochem., 1989, vol. 58, pp. 309-350.

Krieg, P.A., et al., "In Vitro RNA Synthesis with SP6 RNA Polymerase", Methods in Enzymology (1987), pp. 397-415, vol. 155, Academic Press, Inc.

Lamoureux L., et al., "Production of Oligosaccharides in Yogurt Containing Bifidobacteria and Yogurt Cultures" Journal of Dairy Science, vol. 85, pp. 1058-1069, May 2002. American Dairy Science Association, Savoy, IL, US; XP001124200; ISSN: 0022-0302 the whole document, in particular Table 5.

Lawson, P.A., et al., "Recognition of *Fusobacterium nucleatum* subgroups Fn-1, Fn-2 and Fn-3 by ribosomal RNA gene restriction patterns", FEMS Microbiology Letters, vol. 65 (1989), pp. 41-46.

MacCormick, C.A., et al., "Characterization of Variant of the Polysaccharide Acetan Produced by a Mutant of Acetobacter Xylinum Strain CR¼", Journal of Applied Bacteriology (1993), pp. 196-199, vol. 74.

MacFarlane, G.T., et al., "Validation of a Three-Stage Compound Continuous Culture System for Investigating the Effect of Retention Time on the Ecology and Metabolism of Bacteria in the Human Colon", Microbial Ecology (1998), pp. 180-187, vol. 35, New York.

Matsumoto, K., et al., "Galactooligosaccharides", Japanese Technology Reviews, Section E, Chapter 5, (1993), pp. 90-94, vol. 2, 3, Gordon and Breach Science Publishers.

Moller, P. et al., "Intra- and Extracellular β-Galactosidases from Bifidobacterium bifidum and B. infantis: Molecular Cloning, Heterologous Expression, and Comparative Characterization", Applied and Environmental Microbiology, May 2001, pp. 2276-2283.

Olano-Martin, E., et al., "Pectins and Pectic-Oligosaccharides Inhibit *Escherichia coli* O157:H7 Shiga Toxin as Directed Towards the Human Colonic Cell Line HT29", FEMS Microbiology Letters, 218 (2003), pp. 101-105, Elsevier Science B.V.

Onishi, N., et al., "Production of Galacto-Oligosaccharide From Lactose by Sterigmatomyces Elviae CBS8119", Applied and Environmental Microbiology, Nov. 1995, pp. 4022-4025, vol. 61, No. 11, American Society for Microbiology.

Palframan, et al., "Carbohydrate Preferences of *Bifidobacterium* Species Isolated from the Human Gut", Current Issues in Intestinal Microbiology, vol. 4, 2003, pp. 71-75.

Paton, J. et al., "Pathogenesis and Diagnosis of Shiga Toxin-Producing *Escherichia coli* Infections", Clinical Microbiology Reviews, Jul. 1998, pp. 450-479.

Prenosil, J.E., et al., "Formation of Oligosaccharides During Enzymatic Lactose: Part 1: State of Art", Biotechnology and Bioengineering (1987), pp. 1019-1025, vol. 30, John Wiley & Sons, Inc.

Rabiu, B.A. et al., "Synthesis and Fermentation Properties and Novel Galacto-Oligosaccharides by β-Galactosidases from *Bifidobacterium* Species", Applied and Environmental Microbiology, Jun. 2001, pp. 2526-2530, vol. 67, No. 6.

Rowland, I.R., et al., "The Effects of Transgalactosylated Oligosaccharides on Gut Flora Metabolism in Rats Associated With a Human Faecal Microflora", Journal of Applied Bacteriology (1993), pp. 667-674, 674.

Russel P., "IGenetics, Analysis of Gene and Gene Transcripts", Pearson Education, Inc. (2002), pp. 187-189, San Francisco.

Sako, T., et al., "Recent Progress on Research and Applications of Non-Digestible Galacto-Oligosaccharides", International Dairy Journal, vol. 9 (1999), pp. 69-80, Elsevier Science Ltd.

Sambrook, J., et al., "Expression of Cloned Genes in *Escherichia coli*," Molecular Cloning: A Laboratory Manual, vol. 3, Third Edition, 2002, Chapter 15, pp. 15.1-15.65, www.MolecularCloning.com.

Scalabrini, P. et al., "Characterization of Bifidobacterium Strains for Use in Soymilk Fermentation", International Journal of Food Microbiology, Elsevier Science Publishers, Amsterdam, NL, vol. 39, No. 3, 1998, pp. 213-219, XP000952364, ISSN: 0168-1605 the whole document, in particular Table 1.

Schell, M., et al., "The Genome Sequence of Bifidobacterium Longum Reflects its Adaptation to the Human Gastrointestinal Tract", Proceedings of the National Academy of Science, Oct. 29, 2009, pp. 14422-14427, vol. 99, No. 22.

Searle, L., et al., "A mixture containing galactooligosaccharide, produced by the enzymic activity of Bifidobacterium bifidum, reduced *Salmonella enerica* serovar Typhimurium infection in mice", Journal of Medical Microbiology (2009), vol. 58, pp. 37-48.

Seffernick, J.L., et al., "Melamine Deaminase and Atrazine Chlorohydrolase: 98 Percent Identical but Functionally Different", Journal of Bacteriology, Apr. 2001, pp. 2405-2410, vol. 183, No. 8, American Society for Microbiology.

Smeianov et al., GenBAnk accession No. AAG02023, 2000, 2 pages.

(56) References Cited

OTHER PUBLICATIONS

Sweet, D.P., et al., "Quantitative Analysis by Various G.L.C. Response-Factor Theories for Partially Methylated and Partially Ethylated Alditol Acetates", Carbohydrate Research, 40 (1975) pp. 217-225, Elsevier Science Publishers Company, Amsterdam, Belgium.
Tanaka, R., et al., "Effects of Administration of TOS and Bifidobacterium Breve 4006 on the Human Fecal Flora", Bifidobacteria Microflora, 1983, pp. 17-24, vol. 2(1).
Tzortzis, G., et al., "Synthesis of prebiotic galactooligosaccharides using whole cells of a novel strain, Bifidovacterium bifidum NCIMB 41171," Applied Microbiology and Biotechnology, 2005, vol. 68, pp. 412-416, Springer-Verlag, BE.
Tzortzis, G., et al., "A Novel Galactooligosaccharide Mixture Increases the Bifidobacterial Population Numbers in a Continuous In Vitro Fermentation System and in the Proximal Colonic Contents in Pigs in Vivo," The Journal of Nutrition, XP-002560310, American Society of Nutritional Sciences, 2005, pp. 1726-1731.
Van Den Broek. L A M, et al., "Synthesis of α-Galacto-Oligosaccharides by A Cloned α-Galactosidase from Bifidobacterium Adolescentis" Biotechnology Letters, vol. 21, No. 5, May 1999 (May 1999), pp. 441-445, XP009083120; ISSN: 0141-5492 the whole document, in particular p. 443, left-handed column, last paragraph.
Van Laere, K.M., et al., "Characterization of a Novel β-Galactosidase from Bifidobacterium Adolescentis DSM 20083 Active Towards Transgalactooligosaccharides", Applied and Environmental Microbiology, Apr. 2000, pp. 1379-1384, vol. 66, No. 4, American Society for Microbiology.
Van Laere, K.M., et al., "Transglycosidase activity of Bifidobacterium Adolescentis DSM 20083 α-Galactosidase", Applied Microbiology and Biotechnolology, 1999, vol. 52: pp. 681-688, Springer-Verlag, BE.
Vulevic, J. et al., "Modulation of the fecal microflora profile and immune function by a novel trans-galactooligosaccharide mixture (B-GOS) in healthy elderly volunteers", American Journla of Clinical Nutrition, 2008, vol. 88, pp. 1438-1438.
Witowski, A., et al., "Conversion of a β-Ketoacyl Synthase to a Malonyl Decarboxylase by Replacement of the Active-Site Cysteine with Glutamine", Biochemistry 1999, 38, pp. 11643-11650, American Chemical Society.
Yuan, X. et al., "Feruloyl oligosaccharides stimulate the growth of Bifidobacterium bifidum", Anaerobe, vol. 11, 2005, pp. 225-229.
Zarate, S., et al., "Oligosaccharide Formation During Enzymatic Lactose Hydrolysis: A Literature Review", Journal of Food Protection, (Mar. 1990), pp. 262-268, vol. 53, No. 3.
Ziggers, D., "TOS, A New Prebiotic Derived from Whey", Feed Mix, vol. 9, No. 6, 2001, pp. 7-9.
International Search Report dated May 29, 2007 for PCT/GB2007/001081, 3 pages.
International Preliminary Report on Patentability dated Sep. 30, 2008 for PCT/GB2007/001081, 6 pages.
International Search Report dated Apr. 19, 2007 for PCT/EP2006/068029, 2 pages.
International Preliminary Report on Patentability dated May 14, 2008 for PCT/EP2006/068029, 7 pages.
International Search Report dated Aug. 28, 2009, corresponding to PCT/GB2009/001302, 3 pages.
International Search Report dated Jun. 16, 2010 for PCT/GB2010/050659, 3 pages.
International Preliminary Report on Patentability dated Oct. 25, 2011 for PCT/GB2010/050659, 6 pages.
International Search Report dated May 3, 2007 for PCT/GB2006/004796, 4 pages.
International Preliminary Report on Patentability dated Jun. 24, 2008 for PCT/GB2006/004796, 7 pages.
International Search Report dated Jan. 13, 2010 for PCT/GB2009/001329, 3 pages.
International Preliminary Report on Patentability dated Nov. 29, 2011 for PCT/GB2009/001329, 7 pages.
International Search Report dated May 14, 2007 for PCT/GB2007/000178, 4 pages.
International Preliminary Report on Patentability dated Aug. 5, 2008 for PCT /GB2009/000178, 6 pages.
Japanese Office action for JP Patent No. 2006-500267, dated Dec. 9, 2008, and English translation, 9 pages.
Database UniProt [Online] Nov. 1, 1999 (Nov. 1, 1999), "Alpha-galactosidase (EC 3.2.1.22)." XP002431984 retrieved from EBI accession No. UNIPROT:Q9XCX2; Database accession No. Q9XCX2, see sequence.
Database Geneseq [Online] Nov. 19, 2002 (Nov. 19, 2002), "Bifidobacterium longum NCC2705 ORF amino acid sequence SEQ ID No. 919." XP002431983 retrieved from EBI accession No. GSP:ABP66175; Database accession No. ABP66175; see SEQ ID No. 919.
Database UniProt [Online] Sep. 27, 2005 (Sep. 27, 2005), "Glycoside hydrolase, clan GH-D." XP002431985 retrieved from EBI accession No. UNIPROT:Q40Z83; Database accession No. Q40Z83, see sequence.
Database UniProt [Online] Dec. 20, 2005 (Dec. 20, 2005), "Alpha-galactosidase (EC 3.2.1.22)." XP002431987 retrieved from EBI accession No. UNIPROT:Q2XQ11; Database accession No. Q2XQ11, see sequence.
Database EMBL (Online) Oct. 26, 2000, "Bifidobacterium bifidum gene for beta-galactosidase (3701 bp)" 3 pages, XP002429539.
Database UniProt (Online) Mar. 1, 2001, "Beta-galactosidase (EC 3.2.1.23)." 1 page , XP002429540.
Database UniProt [Online] May 30, 2006 (May 30, 2006), "Alpha-galactosidase (EC 3.2.1.22)." XP002431986 retrieved from EBI accession No. UNIPROT:Q1KTD9; Database accession No. Q1KTD9, see sequence.
Database EMBL (Online) Aug. 24, 2004, "Bifidobacterium breve B-galactosidase (B-gal) gene, complete cds" 2 pages XEMBLAY691690.
Newburg, D.S., "Human Milk Glycoconjugates that Inhibit Pathogens", *Current Medicinal Chemistry*, 1999, vol. 6, pp. 117-127.
Coppa, G.B., et al., "Human Milk Oligosaccharides Inhibit the Adhesion to Caco-2 Cells of Diarrheal Pathogens: *Escherichia coli, Vibrio cholerae,* and *Salmonella fyris"*, *Pediatric Research*, 2006, vol. 59, No. 3, pp. 377-382.
Costalos, C., et al., "The Effect of a Prebiotic Supplemented Formula on Growth and Stool Microbiology of Term Infants", *Early Human Development*, 2008, vol. 84, pp. 45-49.
Tauschek, Marija et al.; "Identification of a protein secretory pathway for the secretion of heat-labile enterotoxin by an enterotoxigenic strain of *Escherichia coli*"; PNAS; May 14, 2002; vol. 99; No. 10; pp. 7066-7071.
Todar; Kenneth; "Pathogenic *E. coli*"; Textbook of Bacteriology; Chapter 1; http://textbookofbacteriology.net/e.coli.html; © 2008-2012; 10pp.
International Search Report and Written Opinion of corresponding International Application PCT/GB2009/001329, dated Jan. 13, 2010, 15 pages.
Searle, et al., "A mixture containing galactooligosaccharide, produced by the enzymic activity of Bifidobacterium bifidum, reduces *Salmonella enterica* serovar Typhimurium infection in mice" Journal of Medical Microbiology, vol. 58, No. 1, Jan. 2009 (Jan. 2009), pp. 37-48, XP002560309.
Tzortzis, et al., "A-novel galactooligosaccharide mixture increases the bifidobacterial population numbers in a continuous in vitro fermentation system and in the proximal colonic contents of pigs in vivo" Journal of Nutrition, vol. 135, No. 7, Jul. 2005 (Jul. 2005), pp. 1726-1731, XP002560310.
Gibson, et al., "Dietary modulation of the human colonic microbiota: updating the concept of prebiotics" Nutrition Research Reviews, vol. 17, No. 2, Dec. 1, 2004 (Dec. 1, 2004), pp. 259-275, XP009117209.

\* cited by examiner

METHOD OF PREVENTING DIARRHOEA

CROSS-REFERENCE TO RELATED APPLICATION

This application is a National Phase Patent Application and claims the priority to and the benefit of International Application Number PCT/GB2009/001329, filed on May 27, 2009.

FIELD OF THE INVENTION

The present invention relates to a method for the prevention of the incidence of and/or a reduction in the duration of acute diarrhoea, particularly in travelers, by orally administering an oligosaccharide composition, in particular a non-digestible oligosaccharide composition. The composition preferably comprises a mixture of galactooligosaccharides. Galactooligosaccharides are non-digestible carbohydrates which are resistant to mammalian gastrointestinal digestive enzymes but are fermented by specific colonic bacteria.

BACKGROUND OF THE INVENTION

Diarrhoea in travelers, particularly acute diarrhoea, is one of the most common conditions experienced by individuals travelling abroad to a foreign country, especially to a developing country. Diarrhoea in travelers, hereafter referred to as travelers' diarrhoea or TD, has an attack rate of 20 to 50% and it has been estimated that the disorder can affect over eleven million people annually. In 90% of patients who contract TD, symptoms occur within the first two weeks of travel. It has been shown that bacteria and some viruses are the most common causative agents of TD, with enterotoxigenic *Escherichia coli* (ETEC) being reported as the bacterial cause of 50% of TD cases.

To date, the management of TD has been based on the treatment of the condition using antibiotic and anti-diarrhoea medications such as fluoroquinolones, ciprofloxacin, rifamixin and loperamide. However, these agents can potentially also have an impact on the composition of the commensal gut microflora.

The human gut flora comprises pathogenic, benign and beneficial microbial genera. A predominance of the former can lead to intestinal disorders, that can be both acute, such as travelers' diarrhoea, and chronic, such as inflammatory bowel disease. Attempts have been made to influence the balance of the gut flora in favour of beneficial microorganisms, such as the bifidobacteria, by adding one or more such microbial strains to an appropriate food vehicle such as yoghurt. Such a live microbial feed supplement is known as a probiotic. However, it is difficult to guarantee the survival of live bacteria in foods and also after digestion.

An alternative approach to dietary manipulation of the gut microflora is the use of a prebiotic. Prebiotics are defined as non-digestible food ingredients that beneficially affect the host by selectively stimulating the growth and/or activity of one or a limited number of bacteria in the colon, and which may thus improve the health of the host.

One group of compounds that is classified as prebiotics are the galactooligosaccharides. These are galactose containing oligosaccharides of the form Glc β1-4 [Gal β1-6]$_n$, where n=2 to 5 and are produced from lactose syrup using the transgalactosylase activity of the enzyme β-galactosidase (Chrittenden, (1999) Probiotics: A Critical Review, Tannock, G (ed) Horizon Scientific Press, Wymondham, pp 141-156).

EP 1 644 482 discloses a novel strain of *Bifidobacterium bifidum* that produces a galactosidase enzyme activity that converts lactose to a novel mixture of galactooligosaccharides. This mixture of galactooligosaccharides has been shown to have prebiotic properties and to increase the population of the beneficial bacteria bifidobacteria and lactobacilli.

SUMMARY OF THE INVENTION

In a double blind, placebo controlled, randomised human study, the present inventors have now surprisingly found that oral administration of an oligosaccharide composition results in the prevention of the incidence of and/or a reduction in the duration/severity of acute diarrhoea, particularly in travelers.

The present method has the advantage that the active principle is safe and can be suitably admixed to a drink or food.

In one aspect, the present invention comprises the oral administration of a nutritional composition which reduces the occurrence and/or severity of acute diarrhoea, particularly in travelers.

DETAILED DESCRIPTION OF PREFERRED EMBODIMENTS

The present invention provides a method for the prevention of the incidence of and/or a reduction in the duration/severity of acute diarrhoea, said method comprising orally administering a composition to a mammal, said composition comprising an effective amount of an oligosaccharide.

The oligosaccharide composition may comprise a mixture of galactooligosaccharides, such as the mixture of galactooligosaccharides disclosed in EP 1 644 482. This mixture comprises disaccharides Gal-Gal, trisaccharides Gal-Gal-Glc, a tetrasaccharide Gal-Gal-Gal-Glc and a pentasaccharide Gal-Gal-Gal-Gal-Glc, where Gal represents a galactose residue and Glc represents a glucose residue.

Preferably, the galactooligosaccharide mixture comprises disaccharides Gal (β 1-3)-Glc; Gal (β 1-3)-Gal; Gal (β 1-6)-Gal; Gal (α 1-6)-Gal; trisaccharides Gal (β 1-6)-Gal (β 1-4)-Glc; Gal (β 1-3)-Gal (β 1-4)-Glc; tetrasacchride Gal (β 1-6)-Gal (β 1-6)-Gal (β 1-4)-Glc and pentasaccharide Gal (β 1-6)-Gal (β 1-6)-Gal (β 1-6)-Gal (β 1-4)-Glc. This mixture of galactooligosaccharides is marketed commercially under the name Bimuno (registered trade mark) and is available from Clasado Ltd (Milton Keynes, UK).

Bimuno comprises 49% w/w of galactooligosaccharide. The remainder of the composition may comprise non-active components such as glucose, lactose, acacia gum and citric acid.

The composition may be presented in freeze-dried powder form or as a syrup. It is preferably taken orally on a daily basis. The composition preferably comprises from 1.35 g to 9.6 g of oligosaccharide in 2.75 g to 20 g of the powdered composition, preferably from 1.96 g to 4.9 g of oligosaccharide in 4 g to 10 g of the powder, most preferably 2.7 g oligosaccharide in 5.5 g of composition. This can be taken in a single dose or in two separate doses several hours apart. The composition may be added to a drink, preferably a hot drink, or sprinkled on food.

In order to prevent the incidence of and/or reduce the duration/severity of acute diarrhoea whilst travelling to another country, the composition should preferably be consumed daily by the person travelling for several days prior to departure for a foreign country. Preferably, it should be taken for seven days prior to departure and then every day whilst staying in the foreign country.

Example 1

Freeze-dried powdered composition packaged in a 'stick-pack' and containing per 5.5 g final product:—

| | |
|---|---|
| Galactooligosaccharide (GOS) mixture | 2.67 g |
| Lactose | 1.44 g |
| Monosaccharides (glucose, galactose) | 0.68 g |
| Drying aid | 0.24 g |
| Ash | 0.23 g |
| Protein | 0.05 g |
| Moisture | 0.19 g |

Example 2

Effectiveness of galactooligosaccharides in preventing the incidence and/or reducing the duration of acute diarrhoea in travelers.

Materials and Methods

The study was placebo-controlled, randomised, double blind of parallel design and the target enrolment was healthy volunteers, who would travel and stay in a country of low or high risk for TD for a minimum of 14 days and maximum of 60 days. High risk destinations for incidence of TD included Asia, the Middle East, Africa, Mexico, Central and South America, whereas, low risk areas included Turkey, South Africa and the Caribbean Islands as determined by the Centre for Disease Control and Prevention (CDC, 2008). Recruitment of subjects was conducted through advertisement of the study in the local and national press. Respondents to the advertisement were contacted by telephone and the study was explained to them. A series of screening questions were asked about their holiday, past and current medical conditions, travel details and TD history and concomitant medication, if any. Inclusion and exclusion criteria are given in Table 1. Prohibited medication during the study period included antidepressants, narcotic analgesics, anticholinergic, anti-spasmodic agents for bowel diseases, immunosuppressive drugs and anti-tumour necrosis factors. However, antibiotics, antidiarrheals (such as loperamide) and laxatives were allowed in the case of significant infections as "rescue" medication. Subjects who met the inclusion criteria were sent a volunteer information leaflet and asked to read it thoroughly before taking part. Those who agreed to participate were then randomised into groups with an equal probability of receiving either of the two treatments. This ensured that numbers of subjects allocated to each treatment group were equal after every block of subjects. Following allocation of the participant's number, they were sent a volunteer pack which included: volunteer information leaflet (for reference), consent form, diary card, clinical report form (to be filled in case of diarrheal incidence), instructions of how to consume the product, an explanatory letter for immigration purposes, and the test product or placebo. The product used in this study was prebiotic B-GOS (Bimuno, RTM) (Clasado Ltd, Milton Keynes, UK), served in sachets (5.5 g), once daily, B-GOS is a galactooligosaccharide mixture already marketed in Europe and is generally recognised as safe (GRAS) as defined by United States of America Food and Drug Administration (FDA) (FDA, 2008). The galactooligosaccharide content of B-GOS is 48% (w/w) and its composition in terms of degree of polymerisation (DP) and saccharide linkages have been given previously. The placebo was maltodextrin (oligosaccharide without prebiotic effect) served in sachets (5.5 g), once daily. The interventions were in white aluminium foil sachets blind code labelled. 30 such sachets contained a blank paper box showing all the necessary information such as description of use and researcher contact details were provided to the volunteers at the beginning of the study.

Seven days prior to reaching their final destination, volunteers started consuming the product on a daily basis and kept a daily diary noting the number of bowel movements and average consistency of the stools (formed, loose, water or bloody), as well as occurrences of abdominal discomfort, flatulence, bloating or vomiting. The volunteers continued consuming the treatment whilst on their holidays. The outcome measures that were used for the holiday period, related to:

Number of bowel movements

Stool consistency (1=formed, 2=loose, 3=watery, 4=bloody)

Abdominal pain (0=none, 1=present but well tolerated, 2=present but interfering with but not preventing daily activities, 3=preventing normal daily activities)

Bloating (0=none, 1=present but well tolerated, 2=present and interfering with but not preventing daily activities, 3=preventing normal daily activities)

Flatulence (0=none, 1=present but well tolerated, 2=present and interfering with but not preventing daily activities, 3=preventing normal daily activities)

Vomiting (=absence, 1=presence)

In the case of diarrheal incidence, the volunteer completed a clinical report form describing the signs, symptoms and duration of incidence, hospital admission history, history of exposure and onset, and progress of the diarrheal incidence. Incidence of TD with respect to subjects' age, gender and place of travel in subjects taking prebiotic was compared to the placebo.

Following completion of the study, volunteers were also asked to complete the short World Heath Organisation Quality of Life (WHO-QOL-BREF) questionnaire (post-study questionnaire). This consisted of 22 questions concerning how they felt about their quality of life, health, or other areas of their life during the last four weeks. A scoring system was introduced and scores for each group were calculated based on specific equations as described in WHOQOL-BREF (WHO, 2004). Questions concerned different aspects of subjects' quality of life during their vacation were divided into four domains. Domain 1 related to physical health (daily living activities, dependence on medical substances and medical aids, pain and discomfort, sleep and rest), Domain 2 mainly concerned their psychological condition (positive/negative feelings, self esteem), whereas domain 3 looked at social relationships (personal relationships, social support). Last, domain 4 related to their overall feeling of health as influenced by the environment while being abroad (physical safety, participation in and opportunities for recreation/leisure activities).

Completed diary cards were collected for assessment, along with any unused sachets. Adverse effects were also addressed along with any concomitant medications used.

Ethics

The procedures followed were in accordance with the ethical standards of the Research Ethics Committee of the University of Reading on human experimentation and with the Helsinki Declaration of 1975 as revised in 1983. Ethical approval for the study was granted by the Research Ethics Committee of the University of Reading in July 2007

(approval reference No. 07/21). The study lasted for 9 months.

Statistics

For the power calculation, we predicted that 50% of the subjects would experience diarrhoea and that GOS may reduce this rate by 20%. For 80% power and 5% significance, this gave 93 subjects per treatment group (MGH Biostatistics Software, Massachusetts General Hospital, Boston, Mass.). Statistical analysis was conducted using GENSTAT statistical package version 10.0 (VSN International Ltd). A value of $P<0.05$ was taken to indicate statistical significance. Data were analysed by Fisher's exact text, t-test, ANOVA and multiple regression analysis. In the regression analysis, the dependent variable was one of the outcome measures mentioned above, and independent variables were included, corresponding to the outcome measure for the pre-holiday period. Thus, each subject's bowel score on holiday was analysed and compared between treatments taking into account corresponding pre-holiday scores. Other independent variables were included where appropriate such as duration of travel, TD risk of holiday destination, recent travel history and recent TD.

Results

A total of 201 subjects were recruited and randomised but 42 subsequently did not complete the study, of whom 23 had been allocated to the placebo group and 19 the test (B-GOS) group. Table 5 shows the total number of people who enrolled and finished the study and reasons for not completing. Five subjects did not complete due to adverse reactions and their main complaint was occurrence of mild abdominal pain which was reported during the pre-holiday period.

The distribution of destinations was similar between placebo and prebiotic group (Table 2). Data area presented as average values or percentages of enrolled population. Statistical analysis was performed using ANOVA in Gentstat 10.0 to determine significant differences between groups. In total, 159 subjects completed the study, of which 81 consumed the B-GOS powder and 78 were in the placebo group. Relevant information is summarised in Table 2 concerning the age group (average), sex and previous history of TD.

Bowel habit data for the two time periods (pre-holiday, holiday) in the two groups based on the analysis of the received and completed diaries are given in Table 3 and statistically significant differences indicated. Data presented as average values±standard deviation of enrolled population. Statistical analysis was performed using multiple regression analysis in Gentstat 10.0 to determine significant differences between groups and treatment periods (independent variables included sex, age, duration of travel and high or low risk destination). Regression analysis indicated that the number of bowel movements (average per day) significantly increased during the holiday compared to the pre-holiday period in the placebo group ($p<0.05$), but not in the B-GOS group ($p=0.12$). The average bowel movement number was not significantly different during the holiday period between treatments but it should be noted that the baseline (pre-holiday) number was significantly higher for the B-GOS group when compared to placebo, indicating substantial heterogeneity amongst the interventions as far as the average daily number of bowel movements was concerned. For stool consistency and abdominal pain, significant differences occurred between pre- and holiday periods in the placebo group ($p<0.05$) but not in B-GOS ($p=0.10$). There was no difference ($p=0.23$) between the two treatments during the holiday period. A similar analysis for flatulence and bloating showed that neither the study period nor treatment exerted a significant effect.

The analysis of clinical report forms concerning incidence of diarrhoea and related symptoms, showed a striking effect of B-GOS on the incidence and duration of TD. 31% of persons who took part in the study reported diarrhoea during the holiday period. Data in Table 4 is presented as average values±standard deviation of population experienced diarrhoea or duration of each symptom and were analysed by using Fischer's exact test and multiple regression analysis in Gentstat 10.0 (independent variables: sex, age, duration of travel and high or low risk destination). The data show the incidence and duration of diarrhoea as well as the duration of other symptoms such as abdominal pain, vomiting, fever, anorexia, headache and dizziness. Fisher's exact test indicated that a significantly ($p=0.03$) lower number of volunteers who consumed B-GOS ($n=19$) had diarrheal during the holiday period compared to the placebo group ($n=30$). Regression analysis similarly indicated that the duration of diarrhoea and associated abdominal pain was significantly lower in the B-GOS group when compared to placebo, regardless of destination or holiday duration. There were no other differences in other symptoms between the two treatment groups. 34% of volunteers in the placebo group followed a "relief" treatment (such as Imodium, loperamide or ciprofloxamin) versus 22% in the B-GOS group (data not presented).

Analysis of the overall feeling of subjects, as based on a scoring system, showed that people enrolled in the prebiotic B-GOS group reported better ($P<0.05$) overall feelings concerning their health than those in the placebo group. Analysis of scores (data not presented), showed that the B-GOS group were more satisfied with their health condition compared to the placebo group.

CONCLUSION

The results show striking findings concerning not only the duration but also on the incidence of TD. A significantly lower number of subjects who consumed the prebiotic B-GOS experienced diarrheal episodes during their holiday period compared to the placebo group ($p<0.05$). Similarly, the duration of diarrhoea and abdominal pain were significantly lower in the B-GOS group compared to the placebo ($p<0.05$). In a previous study, the use of another prebiotic (FOS) did not show such an effect (Cummings, et al, 2001, Aliment. Pharmacol. Ther., 15, 1139-1145) as the incidence of diarrhoea and several measures of bowel habit, stool frequency, consistency and size, recorded in the diary, did not demonstrate significant differences between the two groups at any study period. The only significant effect was noticed in flatulence, which significantly increased in the FOS group.

In the current study with B-GOS, a different class of prebiotic molecule, a significant increase in the number of bowel movements, stool consistency and abdominal pain was obtained between pre- and holiday periods for the placebo group but not for B-GOS. This was not unexpected as diarrheal incidence was significantly higher in the placebo group. Additionally, the duration of diarrhoea and abdominal pain were reported to be significantly lower in the group of people that consumed B-GOS compared to placebo.

There will be various modifications, improvements and application of the disclosed invention that will be apparent to those of skill in the art, and the present application encompasses such embodiments to the extent allowed by law. Although the present invention has been described in the context of certain preferred embodiments, the full scope of the invention is not so limited, but is in accordance with the scope of the following claims. All references, patents and other publication are specifically incorporated by reference herein.

TABLE 1

Inclusion and exclusion criteria

| Inclusion Criteria | Exclusion criteria |
|---|---|
| The period of travel should be a minimum of 14 days and a maximum of 60 days | Subject is unwilling to participate |
| | Subject is taking a probiotic and/or prebiotic preparation (outside of study product). |
| Aged 18 years or older | |
| Subjects willing and able to enter data in the diary card | Subject is unable to comply with the protocol |
| Subjects willing and able to take the study supplement as per protocol | Subject suffers from a medical condition that causes regular gastrointestinal symptoms—e.g. irritable bowel syndrome, thryotoxicosis, post-vagotomy, diabetic autonomic neuropathy, malabsorption, short bowel syndrome, Crohn's disease, Coeliac disease, Ulcerative Colitis, previous bowel surgery, cystic fibrosis |
| Subject must have adequate general health (as determined by the investigators) | Subject regularly takes medication that alters gastrointestinal function |
| | Subject is sufffering from diabetes (Type I or Type II) |
| Ability to communicate well with the investigator and to comply with the requirements of the study. | Subject takes long-term antibiotics (e.g. for acne or recurrent urinary infections) |
| | Subject plans to take docycycline as anti-malarial prophylaxis |
| The volunteer has given written informed consent to participate and is willing to participate in the study. | Prophylactic use of Ciprofloxacin |
| | Antibiotics should be avoided whilst subjects are taking the study preparation. However, short-term use of antibiotics in the case of acute illnesses will not be an exclusion criterion |
| | Known allergic reaction to dairy products |
| | Use of any investigational or non-registered drug other than the study supplement within 30 days preceding the first dose of the study supplement |
| | Subject is pregnant or lactating |

TABLE 2

Baseline characteristics of prebiotic GOS and placebo group

| | B-GOS GROUP (n = 81) | Placebo Group (n = 78) |
|---|---|---|
| Age (average) | 38 | 30 |
| High Risk Destination (%) | 91 | 88 |
| Travelled in past 12 months (%) | 76 | 72 |
| Travellers' diarrhoea incidence in past 12 months (5) | 30 | 33 |

TABLE 3

Bowel habit of volunteers by study period and treatment

| Bowel Habit | Period | B-GOS Group (n = 81) | Placebo Group (n = 78) |
|---|---|---|---|
| Movements (avg number/day) | Pre-holiday | 1.373¥ ± 0.514 | 1.146 ± 0.438 |
| | Holiday | 1.286 ± 0.514 | 1.292* ± 0.512 |
| Stool Consistency (avg score/day) | Pre-holiday | 1.157 ± 0.328 | 1.060 ± 0.295 |
| | Holiday | 1.166 ± 0.339 | 1.168* ± 0.379 |
| Abdominal Pain (avg score/day) | Pre-holiday | 0.119 ± 0.206 | 0.116 ± 0.191 |
| | Holiday | 0.183 ± 0.174 | 0.231* ± 0.252 |
| Bloating (avg score/day) | Pre-holiday | 0.227 ± 0.291 | 0.242 ± 0.367 |
| | Holiday | 0.218 ± 0.268 | 0.237 ± 0.337 |
| Flatulance (avg score/day) | Pre-holiday | 0.472 ± 0.477 | 0.488 ± 0.439 |
| | Holiday | 0.436 ± 0.541 | 0.549 ± 0.651 |

*Significant difference between study period ($P < 0.05$)
¥Significant difference between treatments ($P < 0.05$)

TABLE 4

Diarrheal incidence and associated symptoms duration per treatment

| Subjects with diarrheal incidence | 19 | 30* |
|---|---|---|
| Diarrhoea duration (avg number of days) | 2.368 ± 2.060 | 4.567* ± 3.026 |
| Duration of abdominal pain (avg number of days) | 2.000 ± 1.987 | 3.533* ± 2.583 |
| Duration of vomiting (avg number of days) | 0.526 ± 0.722 | 0.433 ± 0.675 |
| Duration of fever (avg number of days) | 0.210 ± 0.713 | 0.133 ± 0.581 |
| Duration of anorexia (avg number of days) | 0.157 ± 0.688 | 0.233 ± 0.466 |
| Duration of headache (avg number of days) | 0.578 ± 0.961 | 0.600 ± 1.695 |
| Duration of dizziness (avg number of days) | 0.663 ± 0.806 | 0.800 ± 1.763 |

*Significant difference between treatments ($P < 0.05$)

Table 5: Shows the number of subjects at each stage of the study

| | Bimuno | |
|---|---|---|
| | Per 100 g | Per 5.5 g |
| Moisture | 3.4 | 0.19 |
| GOS | 48.5 | 2.67 |
| Lactose | 26.2 | 1.44 |
| Monosaccharides | 12.4 | 0.68 |
| Drying aid | 4.3 | 0.24 |
| Ash | 4.3 | 0.23 |
| Protein | 1.0 | 0.05 |

The invention claimed is:

1. A method of reducing the incidence of traveler's diarrhoea in a human, comprising orally administering daily to said human an effective amount of a composition comprising a mixture of galactooligosaccharides wherein the mixture of galactooligosaccharides comprises disaccharides Gal (β 1-3)-Glc; Gal (β 1-3)-Gal; Gal (β 1-6)-Gal; Gal (α 1-6)-Gal; trisaccharides Gal (β 1-6)-Gal (β 1-4)-Glc; Gal (β 1-3)-Gal (β 1-4)-Glc; tetrasaccharide Gal (β 1-6)-Gal (β 1-6)-Gal (β 1-4)-Glc and pentasaccharide Gal (β 1-6)-Gal (β 1-6)-Gal (β 1-6)-Gal (β 1-4) Glc for a period of seven days prior to departure and each day during travel away from home, wherein the effective amount of the composition comprises 2.7 g of the galactooligosaccharides in 5.5 g of the composition, and wherein the composition is administered as a single daily dose.

2. A method of reducing the incidence of traveler's diarrhoea in a human, comprising orally administering daily to said human an effective amount of a composition comprising a mixture of galactooligosaccharides wherein the mixture of galactooligosaccharides comprises disaccharides Gal (β1-3)-Glc; Gal (β1-3)-Gal; Gal (β1-6)-Gal; Gal (α 1-6)-Gal; trisaccharides Gal (β 1-6)-(Gal (β 1-4)-Glc; Gal (β 1-3)-Gal (β 1-4)-Glc; tetrasaccharide Gal (β 1-6)-Gal (β 1-4)-Glc and pentasaccharide Gal (β 1-6)-Gal (β 1-6)-Gal (β 1-4) Glc; wherein the effective amount of the composition comprises 2.7 g of the galactooligosaccharides, 1.44 g of lactose and 0.68 g of monosaccharides in 5.5 g of the composition.

3. A method of maintaining bowel movement number, stool consistency and abdominal pain in a human, comprising orally administering daily to said human an effective amount of a composition comprising a mixture of galactooligosaccharides wherein the mixture of galactooligosaccharides comprises disaccharides Gal (β1-3)-Glc; Gal (β1-3)-Gal; Gal (β1-6)-Gal; Gal (α 1-6)-Gal;

trisaccharides Gal (β 1-6)-(Gal (β 1-4)-Glc; Gal (β 1-3)-Gal (β 1-4)-Glc; tetrasaccharide Gal (β1-6)-Gal (β 1-4)-Glc and pentasaccharide Gal (β 1-6)-Gal (β 1-6)-Gal (β 1-4) Glc for a period of seven days prior to departure and each day during travel away from home, wherein the effective amount of the composition comprises 2.7 g of the galactooligosaccharides in 5.5 g of the composition.

* * * * *